United States Patent [19]

Cohen

[11] Patent Number: 4,599,081
[45] Date of Patent: Jul. 8, 1986

[54] ARTIFICIAL HEART VALVE

[76] Inventor: Fred M. Cohen, 2601 E. Vogel Ave., Phoenix, Ariz. 85028

[21] Appl. No.: 430,403

[22] Filed: Sep. 30, 1982

[51] Int. Cl.[4] ............................ A61F 2/24; A61F 2/22
[52] U.S. Cl. .................................... 623/2; 137/512.1;
  137/516.11; 623/3
[58] Field of Search .................. 3/1.5, 1.7; 137/512.1,
  137/516.11; 623/2, 3

[56] References Cited

U.S. PATENT DOCUMENTS

| 3,416,159 | 12/1968 | Smeloff et al. | 3/1.5 |
| 3,451,067 | 6/1969 | Jordon | 3/1.5 |
| 3,570,014 | 3/1971 | Hancock | 3/1.5 |
| 3,594,824 | 7/1971 | Nakib | 3/1.5 |
| 3,689,942 | 9/1972 | Rapp | 3/1.5 |
| 3,791,769 | 2/1974 | Kovacs | 3/1.5 |
| 3,812,542 | 5/1974 | Shiley | 3/1.5 |
| 3,858,246 | 1/1975 | Milo | 3/1.5 |
| 3,996,623 | 12/1976 | Kaster | 3/1.5 |
| 4,218,782 | 8/1980 | Rygg | 3/1.5 |
| 4,275,469 | 6/1981 | Gabbay | 3/1.5 |

FOREIGN PATENT DOCUMENTS

2419926  1/1975  Fed. Rep. of Germany ........... 3/1.5

Primary Examiner—Ronald L. Frinks
Attorney, Agent, or Firm—Charles P. Padgett, Jr.

[57] ABSTRACT

An artificial heart valve of turbine-like construction includes a rotor that translates and rotates to cause a plurality of rotor blades to either occlude or unocclude spaces between adjacent ones of a plurality of stator blades.

31 Claims, 15 Drawing Figures

ARTIFICIAL HEART VALVE

BACKGROUND OF THE INVENTION

1. Field of the Invention

This invention relates generally to medicine and more specifically to an artificial heart valve.

2. Description of the Prior Art

When a person's heart is damaged by either a congenital malformation or a disease, a surgical procedure is often used to excise a defective valve from the heart and implant an artificial heart valve. The first time the procedure was used was in 1961.

The most often used artificial heart valves fall into four major categories and have been implanted with varying degrees of success. The four categories include what are known as a ball valve, a tilting disc valve, a leaflet valve and a tissue valve.

The ball valve, which was implanted during the early years of the procedure, is of a type reported to have been used as a stopper on bottles during the nineteenth century. The ball valve includes an annular metal ring, known as an orifice ring, attached to a cage that houses either a solid or a hollow ball. The orifice ring is connected on its outer surface to what is known as a suture ring, which is typically made from a fabric. The suture ring is sewn into a tissue annulus in the anatomic position of the excised defective valve.

In response to a differential blood pressure across the orifice ring in a backward direction, the ball moves to seat itself against the orifice ring to inhibit a flow of blood in the backward direction. In response to a differential blood pressure across the orifice ring in a forward direction, the ball moves away from the orifice ring to allow a flow of blood in the forward direction.

The ball valve is inherently symmetrical. Because of the symmetry, the blood is symmetrically dispersed about the ball when flowing through the orifice ring, thereby providing a spatially symmetrical velocity distribution of blood around the ball. Because of the inherent symmetry there is no preferred orientation about the axis of the orifice ring when the ball valve is implanted. Therefore, the inherent symmetry is a desirable feature of the ball valve.

The ball valve has undesirable features, such as a high profile caused by the cage being large, and the ball being moved through a large displacement to achieve a desired flow of blood. Additionally, the orifice ring must generally be thick enough to seat the ball. The thickness of the orifice ring reduces what is known as an orifice-to-annulus diameter ratio. It is desirable for an artificial heart valve to have a high orifice-to-annulus diameter ratio to decrease valvular resistance to a flow of blood. Moreover, it is documented that the movement of the ball may cause the ball valve to have a higher dislodgement rate than other types of artificial heart valves.

When, for example, the ball valve is implanted in the mitral position, there may be an undesirable ventricular impingement during a contraction of tissue around the cage. When the ball valve is implanted in the aortic position, where there is a narrow aortic root, the area between the ball and the aortic wall provides less than the desired flow of blood. In other words, in the aortic position the ball valve may have a high valvular resistance. Additionally, there may be turbulence on the outlet side of the ball valve that results in a thrombus (blood clot) being formed.

An undesirable audible noise may be emitted when the ball is positioned against the orifice ring. Moreover, there is usually stasis (insufficient blood movement) near a margin or interface where the suture and orifice rings meet. Stasis may cause a thrombus, which if dislodged, may result in an embolism in another part of the body of the person, thereby causing serious medical problems. When the person has a ball valve implant, anticoagulants are administered to increase the time required for the blood to clot, thereby reducing thromboembolic complications.

It should be understood that in the ball valve, as in all other artificial heart valves, the size depends upon the size of the tissue annulus. When the ball valve is large and the person has a low cardiac output, there is an increased probability of stasis. Conversely, when the ball valve is small and the person has a high cardiac output, there is an increased probability of turbulence. It should be appreciated that flow rate through the ball valve in the aortic position is on the order of three times the flow rate through the ball valve in the mitral position.

After the implantation, endothelial tissue ideally grows into the suture ring, up to the margin of the suture and orifice rings. The endothelial tissue is durable and serves to maintain the ball valve in the anatomic position. Completion of the endothelial growth takes from six months to two and one half years. However, the first stage of the endothelial growth is a thrombus formation.

It is well-known that endothelial tissue does not adhere to the orifice ring. The orifice ring may cause a rejection reaction whereby either an excess endothelial tissue growth or thrombus formation partially encapsulates the orifice ring, thereby interfering with the operation of the ball valve. Additionally, since the first stage of endothelial growth is the thrombus formation, the excess endothelial growth may result in a thromboembolic event.

Efforts have been made to eliminate the margin by covering the orifice ring with a fabric. When this is done, there is an incidence of fabric wear causing the fabric to be dislodged by the ball before the completion of the endothelial tissue growth, thereby causing serious medical problems.

More recently, the procedure has been used to implant what is known as a tilting disc valve, which includes a disc having a diameter substantially equal to the interior diameter of the orifice ring. The disc is tiltably connected to the orifice ring along a chord that intersects about 120 degrees of arc of the disc and the orifice ring. The orifice ring is connected to the suture ring as described hereinbefore.

In response to the differential blood pressure in the backward direction, the disc tilts about the 120 degree chord to seat itself to substantially occlude the orifice of the orifice ring to inhibit the flow of blood in the backward direction. In response to the differential blood pressure in the forward direction, the disc tilts approximately 60 degrees about the 120 degree cord. The tilting unseats the disc to form a small opening, along 120 degrees of arc of the orifice ring, and a large opening along 240 degrees of arc of the orifice ring. Blood flows in the forward direction through the small and the large openings.

Because the disc tilts only 60 degrees, the flow of blood through the large opening is deflected from a path that is parallel to the axis of the orifice ring, which may cause an undesirably high valvular resistance. Additionally, the flow of blood through the small and large openings has differing velocity distributions which may cause turbulence that results in a thrombus being formed.

Since the disc tilts about the 120 degree chord, the tilting disc valve is substantially asymmetrical. Because of the asymmetry, there is a preferred orientation about the axis of the orifice ring when the tilting disc valve is implanted. Surgeons have differing preferences of orientation. Additionally, the disc moves through an undesirably large displacement to achieve the desired flow of blood, thereby causing the tilting disc valve to have a high profile when the disc is tilted.

The tilting disc valve, like the ball valve, may emit an undesired audible sound when the disc is seated against the orifice ring. Moreover, there is often stasis across the 120 degree chord as well as near the margin of the suture and orifice rings near the 120 degree chord. When the person has a tilting disc valve implant, anticoagulants are administered to reduce thromboembolic complication of the type referred to in connection with the ball valve.

Similar to the ball valve, either the excess endothelial tissue growth or thrombus formation may partially encapsulate the orifice ring of the tilting disc valve. The partial encapsulation may seriously interfere with the operation of the tilting disc valve.

The surgical procedure has additionally been used to implant what is known as a leaflet valve. A flexible fabric-like material, in the shape of a disc is connected along a diameter to a thin, rigid rod, thereby forming a pair of semi-circular, moveable leaflets. The ends of the rod are respectively connected to diametrically opposite locations on the orifice ring.

In response to the differential blood pressure in the backward direction, the edges of the leaflets are seated against the orifice ring to inhibit the flow of blood in the backward direction. In response to the differential blood pressure in the forward direction, the leaflets tilt in opposite directions about the rod, away from the orifice ring, to allow the flow of blood in the forward direction.

Like the artificial heart valves described hereinbefore, when the leaflet valve is small, there may be turbulence on its outlet side that results in a thrombus being formed. Additionally, the leaflets do not usually move sufficiently far from the orifice ring to achieve the desired flow of blood. Moreover, there is usually stasis near the rod.

There are other types of leaflet valves where leaflets are independently hinged. A leaflet valve of this type usually has an undesired projection from the inlet side of its orifice ring.

The independently hinged leaflets may achieve a desired flow of blood in the forward direction. However, the independently hinged leaflets may not close simultaneously, thereby causing turbulence that results in a thrombus being formed. Additionally, one of the independently hinged leaflets may fail to close, thereby causing a serious medical problem. When the person has a leaflet valve implant, the anticoagulants are administered to reduce thromboembolic complications of the type referred to hereinbefore.

It should be appreciated that the leaflet valves have only two axes of symmetry. Hence, the leaflet valves are substantially asymetrical.

Often when the person has a contra-indication to anticoagulants, such as a bleeding ulcer, or pregnancy, administering the anticoagulants can be fatal. To obviate a need for the anticoagulants, the procedure is used to implant either a human, porcine or bovine semi-lunar cusp tissue valve. The suture ring is sewn to the tissue valve, thereby forming a cloth-tissue margin.

When the tissue valve is implanted, there is a reduced rejection reaction that reduces the incidence of excess endothelial growth and thromboembolic complications without administering the anticoagulants. For this reason, tissues of the tissue valve are referred to in the art as thrombogenic resistant.

Although the tissue valve obviates the need for anticoagulants, the tissue valve has disadvantages not shared by the artificial heart valves described hereinbefore. The cusps of the tissue valve may not close or open either simultaneously or completely. Additionally, the tissue valve has a high profile and may have a high valvular resistance.

The tissue valve often hardens and becomes partially inoperative, due to fibrosis and/or calcification, within three to five years of its implantation. Because of the hardening, the tissue valve becomes inoperative and is frequently replaced.

It should be appreciated that an artificial heart valve performs on the order of 40,000,000 openings and closings per year, thereby subjecting most components thereof to wear. Accordingly, tissues of the tissue valve cannot be used as a cover for the orifice ring of either the ball, tilting disc or leaflet valves to reduce the need for anticoagulants; the disc, the ball or leaflets would wear away the cover.

In accordance with the explanation given hereinbefore, implantation of an artificial heart valve of the prior art often undesirably exposes the person to risks of thrombus formation due to either stasis or turbulence, and excess endothelial tissue growth that interferes with operation of the artificial heart valve. Moreover, anticoagulants must either be administered to the person or the person must be subjected to frequent replacement of the artificial heart valve. There is a need for an artificial heart valve that has the best properties of known types of artificial heart valves without the disadvantages thereof.

SUMMARY OF THE INVENTION

One object of the present invention is to provide an improved artificial heart valve.

It is a further object of the invention to provide an artificial heart valve that does not have stasis near the margin of its suture and orifice rings.

Yet another object of the present invention is to provide an artificial heart valve in which insufficient blood movement or stasis, particularly near the margin or interface between the orifice ring and the suture ring, is substantially eliminated (1) to greatly reduce the chance of thrombus and/or thromboembolism; (2) to substantially eliminate excess endothelial growth; (3) to significantly reduce the risk of a rejection reaction; and (4) to substantially eliminate the need for anticoagulants.

It is yet a further object of the present invention to provide an artificial heart valve in which turbulence and stasis and the risk of a resulting thromboembolic event is further reduced by the use of a symmetrical valve structure; by a significant reduction in turbulence resulting from the use of a relatively low valvular resistance, a relatively high orifice-to-annulus diameter ratio, the blood movement itself, and a flow of blood having spatially distributed equal velocities.

It is another object of the present invention to provide an artificial heart valve which has a very high speed occluder, substantially no noise, almost no chance of fatigue failure due to the equal distribution of stress over the rotor and stator, and no potentially harmful projections.

Another object of the present invention is to provide an artificial heart valve having a low profile.

It is still a further object of the present invention to provide an artificial heart valve in which at least a portion of the orifice ring is covered with thrombogenic resistant tissue which is not subject to wear.

It is yet another object of the present invention to provide an artificial heart valve in which a relatively low fatigue-resistant but high thrombogenic resistant material such as human, bovine or porcine pericardial tissue is used as an orifice ring covering which is not subject to wear for solving the problems listed hereinabove.

Still another object of the present invention is to provide an artificial heart valve that may be implanted with a reduced risk of causing thromboembolic complications.

Another object of the present invention is to provide an artificial heart valve where a flow of blood therethrough has a symmetrical velocity distribution on its outlet side.

Another object of the present invention is to provide a symmetrical artificial heart valve.

Another object of the present invention is to provide an artificial heart valve that is useable in an artificial heart.

According to the present invention, a rotor moves relative to a stator to provide a high resistance to a flow of blood in response to a differential blood pressure in a backward direction; said rotor moves to provide a low resistance to the flow of blood in response to a differential blood pressure in a forward direction.

An artificial heart valve in accordance with the present invention has a high degree of symmetry and has a lower profile than those of the prior art. Moreover, it does not have components that move through large displacements, and provides a reduced risk of stasis and turbulence when implanted. The flow of blood therethrough is substantially parallel to the axis of an orifice ring.

Reference is hereby made to my previous written description entitled "Improvement In Artificial Heart Valves For Human Implantation" which was filed under the Disclosure Document Program on July 30, 1982, and assigned Disclosure Document No. 110138, which is incorporated by reference herein.

The foregoing and other objects, features, and advantages of the invention will be apparent from the following, more particular description of the preferred embodiment of the invention, as illustrated in the accompanying drawings.

DESCRIPTION OF THE PREFERRED EMBODIMENT

Referring to FIGS. 1–4 and 8, an artificial heart valve 10 is of turbine-like construction and has a stator that includes similar rigid stator blades 12 and 14 each having the general shape of a turbine blade. Each of the stator blades 12 and 14 has one edge connected to a vertical projection 15. The projection 15 is explained hereinafter.

The stator blades 12 and 14 are all fixedly connected at their proximal radially inner ends to a stator hub 16 (FIGS. 2 and 7) that is symmetric about a central axis 17. The axis 17 is the central axis of the valve 10. The stator hub 16 has a flat-faced top and a cone-shaped bottom. The cone-shaped bottom inhibits stasis that could occur if the bottom of the stator hub 16 were flat.

There is a known angle, that varies with distance from the axis 17, between the plane of the face of the stator hub 16 and the stator blades 12 and 14. In an alternative embodiment, the known angle does not vary with distance from a central axis.

Figure 3:
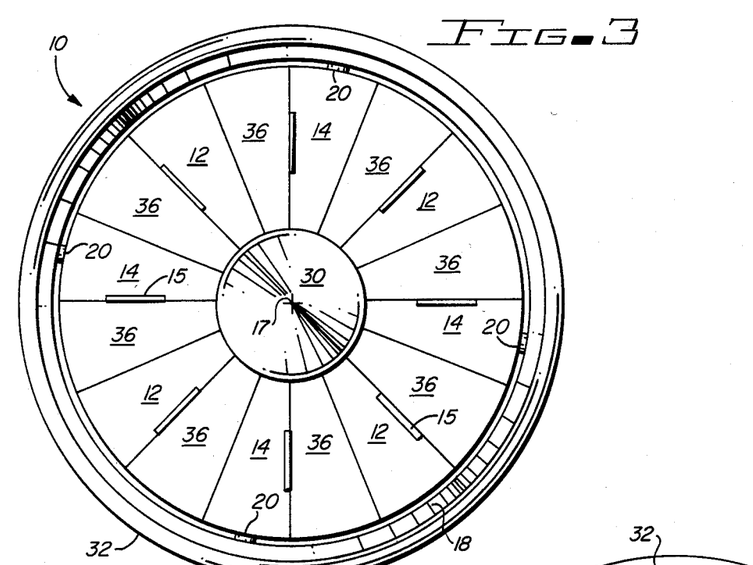
FIG. 3 is a plan view of the artificial heart valve of FIG. 1 in its closed position.
Figure 4:
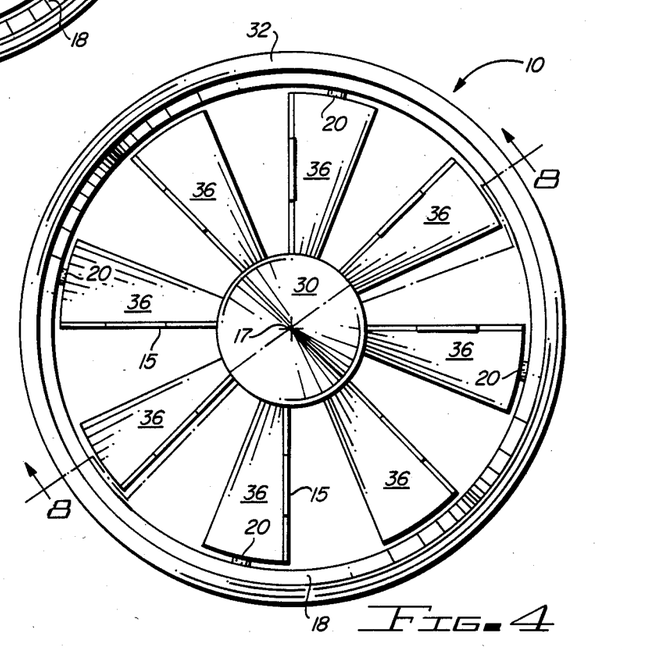
FIG. 4 is a plan view of the artificial heart valve of FIG. 2 in its open position.

The stator blades 12 and 14 are equally spaced about the stator hub 16. As best shown in FIGS. 3 and 4, the top projected view of the space between adjacent ones of the stator blades 12 and 14 is substantially the same as the top projected view of the stator blades 12 and 14.

Correspondingly, the side projected view of the space, taken in a plane through the center line of the space, is substantially the same as the side projected view of one of the stator blades 12 and 14 taken in a plane along the center line thereof. As explained hereinafter, the space between the stator blades 12 and 14 has the projected views to provide for closing of the valve 10. The stator blades 12 and 14 are either integral to the stator hub 16 or connected thereto in any suitable manner. Generally, there are "n" stator blades, where the n≧2 and "n" is a positive whole number.

The stator blades 14 are fixedly connected at their distal, radially outer ends to a rigid orifice ring 18 via rods 20 (FIG. 3). The orifice ring 18 is in axial alignment with the axis 17 whereby the orifice ring 18 and the stator hub 16 are substantially coaxial thereto. The orifice ring includes an orifice inlet aperture or inlet 13, and orifice outlet aperture or outlet 15, and a hollow central chamber or channel 11 interconnecting the inlet and the outlet.

In this embodiment, the orifice ring 18 is covered or at least partially covered with a bovine pericardial tissue, a thrombogenic resistant material. In alternative embodiments, an orifice ring may be completely or partially covered with a thrombogenic resistant material such as either porcine or human pericardial tissues or pyrolytic carbon.

As explained more fully hereinafter, the orifice ring 18 is not subjected to wear from either flexion or from physical contact with the rotor or occluder itself. Therefore, the thrombogenic resistant covering is not subjected to wear and hence is fatigue resistant and safely provides a reduced probability of causing either a thromboemoblism or an excess endothelial tissue growth that could interfere with the operation of the valve 10. The thrombogenic resistant covering forms an interface at the margin of the orifice ring 18 and a suture ring 32 that eliminates the need for the anticoagulants for reasons given hereinbefore in connection with the description of the tissue valve however unlike the previous description of the tissue valve, the orifice ring is not subject to wear or fatigue for the reasons previously and hereinafter given.

It should be understood that in the present invention, any combination of materials may be used to construct an orifice ring having suitable fatigue and thrombogenic resistant properties. In another alternative embodiment, the thrombogenic resistant material may be used to cover all or part of a suture ring 32 in addition to covering all or part of an orifice ring 18 individually or collectively.

Figure 6:
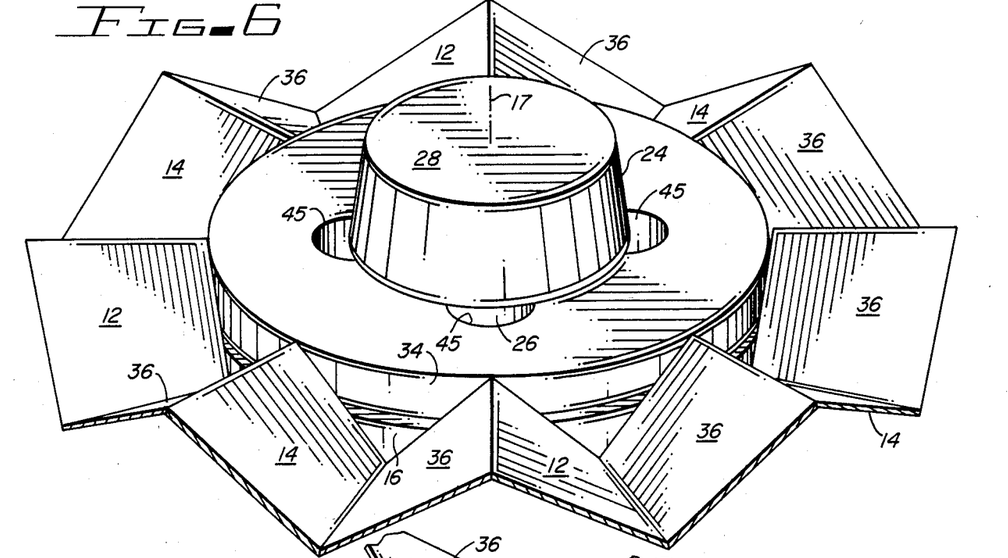
FIG. 6 is an isometric view showing the artificial heart valve of FIG. 1 in its closed position, with portions broken away.
Figures 7, 8:
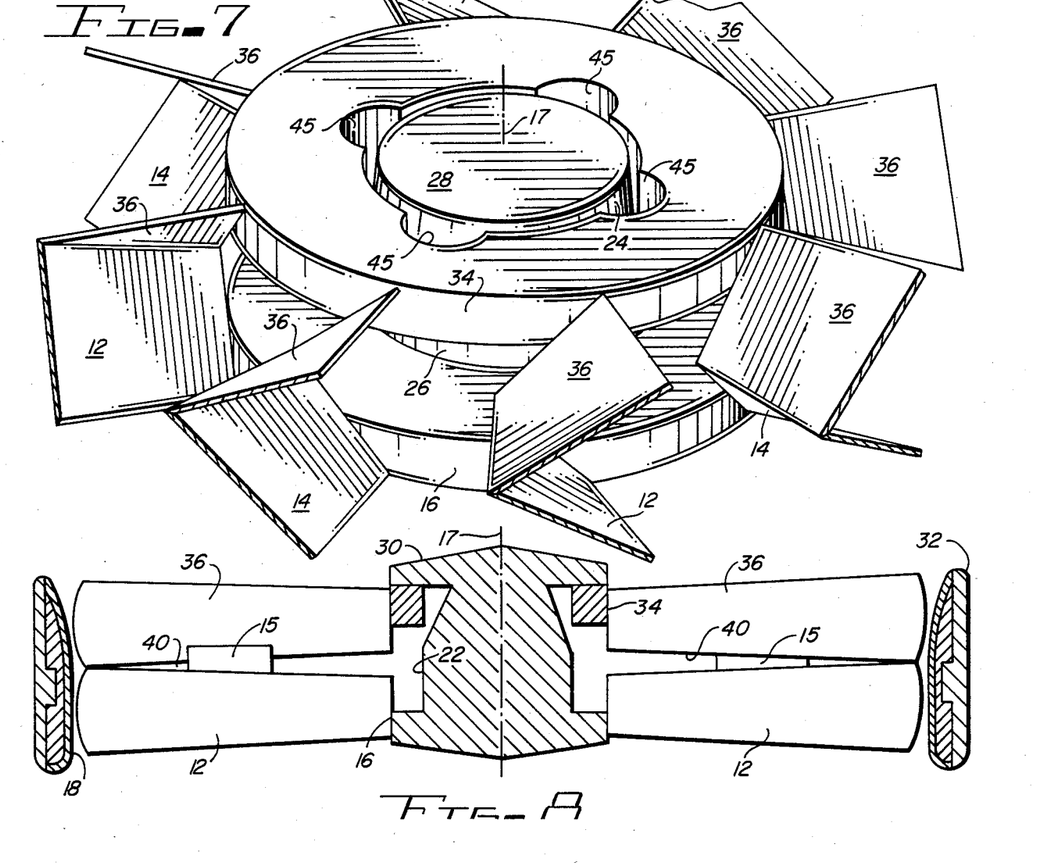
FIG. 7 is an isometric view showing the artificial heart valve of FIG. 1 in its open position, with portions broken away.
FIG. 8 is a sectional view of FIG. 4 taken along the line 8—8 thereof, with portions broken away.

Referring to FIGS. 6 and 7, the stator additionally includes a post 22 having a top section 24 in the shape of a right truncated cone and a bottom section 26 in the shape of a cylinder. The bottom section 26 is longer than the top section 24 for reasons explained hereinafter. The sections 24 and 26 are integrally and coaxially connected to each other. The bottom section 26 is integrally and coaxially connected at its distal end to the stator hub 16 (FIG. 8), whereby the post 22 is in axial alignment with the axis 17. An end surface 28 of the top section 26 is fixedly and coaxially connected in any suitably manner to a collar 30, whereby the collar 30 is in axial alignment with the axis 17.

The collar 30 has a cone-shaped top and a flat-faced bottom. The cone shape inhibits stasis that could occur if the top of the collar 30 were flat.

The orifice ring 18 is fixedly connected to a suture ring 32 that is normally made from a fabric that encapsulates a heat shrinkable material. The suture ring 32 is preferably heat shrunk around the periphery of the orifice ring 18, thereby providing the valve 10 with an orifice-to-annulus diameter ratio at least as high as that of any artificial heart valve known in the prior art. In an alternative embodiment, a suture ring is sewn onto an orifice ring or attached thereto in any other suitable manner.

The suture ring 32 is sewn into a tissue annulus formed by an excision of a defective heart valve from a person, whereby the valve 10 is implanted in the anatomic position of the excised valve. Since the suture ring 32 is an element of the stator and there is a fixed connection between all of the elements of the stator, the stator is in a fixed position when the valve 10 is implanted.

The valve 10 has a rotor comprised of an annular rotor hub 34 that is rotatably mounted on the post 22 and substantially coaxial therewith, whereby the rotor hub 34 is rotatable about the axis 17. Additionally, the rotor hub 34 is moveable in translation along the axis 17.

The rotor additionally includes rotor blades 36 of substantially the same size and equal in number to the stator blades 12 and 14. Therefore the projected views of the rotor blades 36 is substantiallly the same as the projected views of the stator blades 12 and 14. Generally, there are "m" rotor blades, where m≧2 and "m" is a positive whole number. Furthermore, the number of rotor blades "m" is generally equal to the number of stator blades "n" such that m=n.

Figure 5:
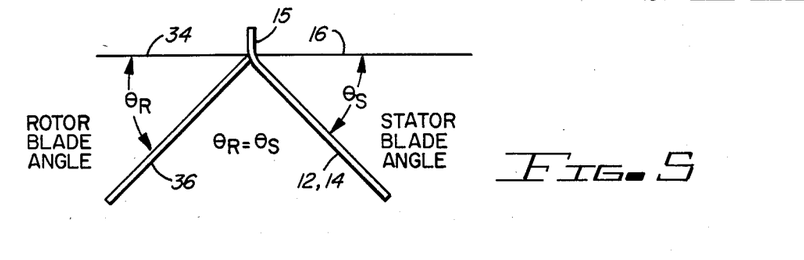
FIG. 5 is a schematic diagram showing the angles between the stator and rotor blades and the faces of stator and rotor hubs, respectively, at a given distance from the central axis of the artificial heart valve of FIG. 1.

The rotor blades 36 are all connected at their proximal, radially inward ends to the rotor hub 34 at a known angle to the face thereof. As shown in FIG. 5, the known angle of the rotor blades 36 is equal to the known angle of the stator blades 12 and 14 but opposed thereto in angular orientation. The known angle of the rotor blades 36 equals the known angle of the stator blades 12 and 14 at any given distance from the axis 17.

The post 22 and the rotor hub 34 maintain the distal ends of the blades 36 in close proximity to the orifice ring 18. However, the blades 36 do not contact the orifice ring 18. Therefore the orifice ring 18 is not subjected to wear.

Figure 1:
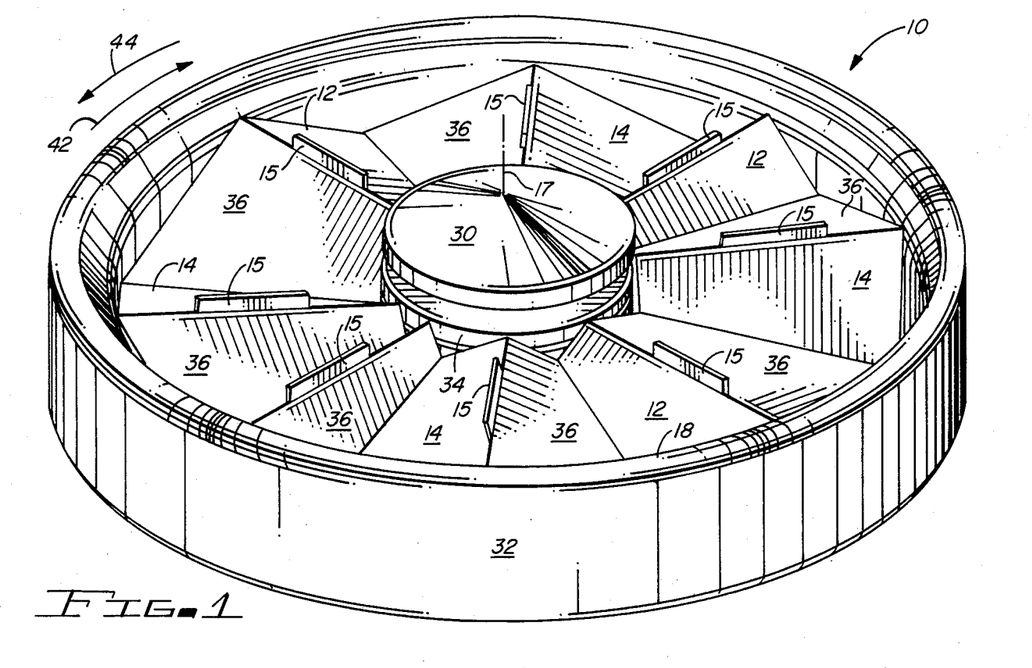
FIG. 1 is an isometric view showing the artificial heart valve of the present invention in its closed position.

Because of the projected views of the rotor blades 36 and the space between adjacent ones of the stator blades 12 and 14, the rotor is operable to position the rotor blades 36 to substantially occlude the spaces between the stator blades 12 and 14, whereby the rotor is in its closed position and the valve 10 is closed (FIGS. 1, 3 and 6). The rotor operates to close the valve 10 in response to a differential blood pressure in a backward direction indicated by an arrow 38.

Figure 2:
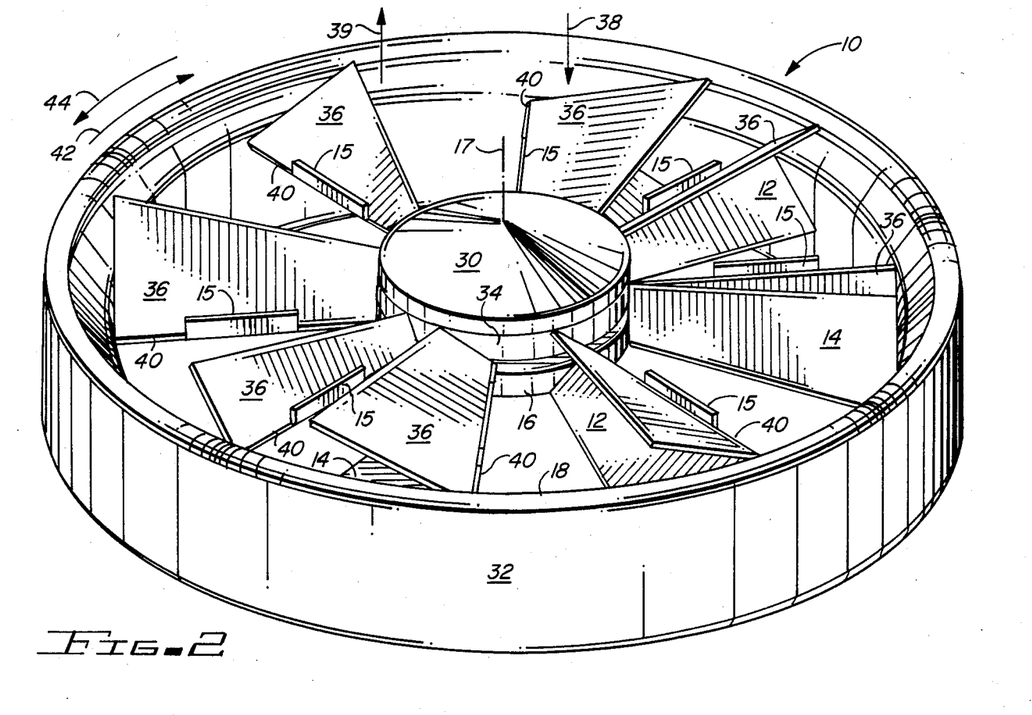
FIG. 2 is an isometric showing view the artificial heart valve of FIG. 1 in its open position.

When the rotor moves to its closed position, there is a translation of the rotor hub 34 away from the collar 30. Additionally there is a rotation of the rotor hub 34 in the direction of an arrow 42 (FIGS. 1 and 2).

Figure 9:
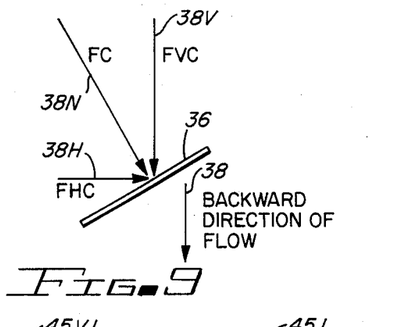
FIG. 9 is a schematic representation of forces that cause the artificial heart valve of FIG. 1 to close.

As shown more particularly in FIG. 9, a blood pressure in the backward direction causes a force on the blades 36 in a direction indicated by an arrow 38N (FC) perpendicular to the rotor blades 36. The force in the direction indicated by the arrow 38N may be resolved in a horizontal direction indicated by an arrow 38H (FHC) and in a vertical direction indicated by an arrow 38V (FVC) that respectively cause the rotation in the direction of the arrow 42 and the translation away from the collar 30. During the translation and the rotation of the rotor to its closed position, edges 40 of the rotor blades 36 sweep past the surface of respective stator blades 12 and 14 thereby causing blood movement that reduces stasis.

It should be understood that because the bottom section 26 (FIGS. 6 and 7) is longer than the top section 24, the rotor blades 36 cannot strike the stator hub 16 when the rotor moves to its closed position. Moreover, when the valve 10 is closed, there is a space between the distal ends of the blades 12, 14 and 36 and the orifice ring 18 that enables a small flow of blood in the direction of the arrows 38, thereby reducing stasis at the margin of the orifice ring 18 and suture ring 32.

The translation away from collar 30 and the rotation in the direction of the arrow 42 is limited by contact between edges 40 with edges of the stator blades 12 and 14, thereby preventing contact between opposed surfaces of the hubs 16 and 34 (FIG. 7). When the valve 10 is open, the edges 40 and the edges of the stator blades 12 and 14, subtend an angle of three to five degrees, as best shown in FIG. 8, to limit contact between the edges 40 and the blades 12 and 14. It should be understood that the surface area of contact between elements of the valve 10 is directly related to hemolysis (blood cell damage) caused by the valve 10.

Correspondingly, the rotor is operable to position the rotor blades 36 to unocclude the spaces, whereby the rotor is in its open position and the valve 10 is open (FIGS. 2, 4, 7 and 8). The rotor operates to open the valve 10 in response to a differential blood pressure in a forward direction, indicated by an arrow 39.

When the rotor moves to its open position, there is a translation of the rotor hub 34 towards the collar 30, and a rotation of the rotor hub 34 in the direction of an arrow 44. The translation towards the collar 30 is limited by contact between opposed surfaces of the collar 30 and the rotor hub 34. The rotation in the direction of the arrow 44 is limited by contact between the edges 40 with respective ones of the projections 15.

Figure 10:
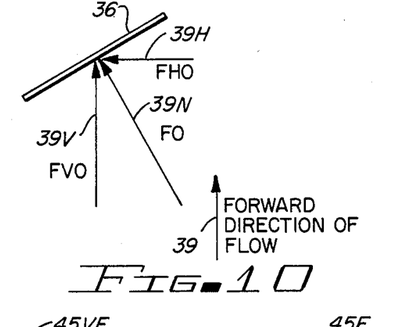
FIG. 10 is a schematic representation of forces that cause the artificial heart valve of FIG. 1 to open.

As shown more particularly in FIG. 10, a blood pressure in the forward direction causes a force on the blade 36 in a direction indicated by an arrow 39N (FO) perpendicular to the rotor blades 36. The force indicated by the arrow 39N may be resolved in a horizontal direction, indicated by an arrow 39H (FHO), and in a vertical direction by an arrow 39V (FVO) that respectively cause the rotation in the direction of the arrow 44 and the translation towards the collar 30. During the translation and the rotation of the rotor to its open position, the edges 40 sweep past the surface of respective stator blades 12 and 14 thereby causing blood movement that reduces stasis.

When the valve 10 is open, most of the flow of blood therethrough is near the orifice ring 18, where the largest space exists between adjacent one of the stator blades 12 and 14. Therefore, unlike artificial heart valves of the prior art, there is a reduced probability of stasis near the orifice ring 18.

Figure 11:
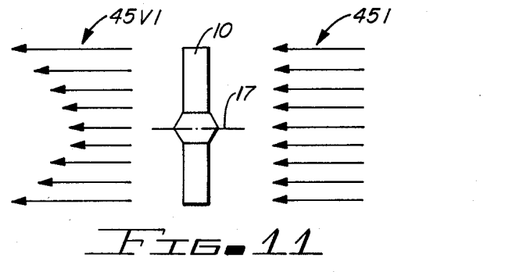
FIG. 11 is a schematic representation of a velocity distribution of blood at the outlet side the artificial heart valve of FIG. 2 in response to an inlet flow of blood having spatially distributed equal velocities.

As shown in FIG. 11, in response to a flow of blood having spatially distributed equal velocities, 45I, (as expected when the valve 10 is implanted in the mitral position and the person has atrial fibrillation) the valve 10 provides a flow of blood having spatially distributed velocities represented by a plurality of arrows 45VI, lengths thereof being representative of the velocity of the flow of blood. It should be appreciated that there is a maximum velocity of flow near the orifice ring 18 because the valve 10 has the least resistance to flow near the orifice ring 18.

Figure 12:
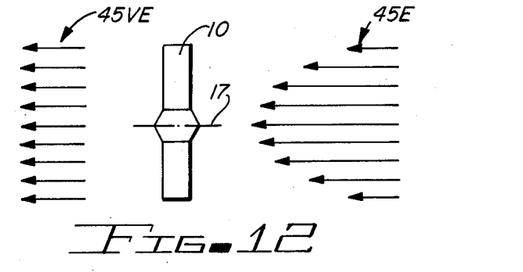
FIG. 12 is a schematic representation of a velocity distribution of blood at the outlet side of the artificial heart valve of FIG. 2 in response to an inlet flow of blood having spatially distributed unequal velocities.

As shown in FIG. 12, blood flowing towards the valve 10 is expected to have a spatial distribution of velocity represented by a plurality of arrows 45E when the person has a normally contracting atrium and ventricle. Accordingly, blood flowing towards the valve 10 has its highest and lowest velocities near the center and edges, respectively, of a contracting atrium or ventricle that pumps the blood. Since the valve 10 has the least resistance to flow near the orifice ring 18, the flow of blood represented by the arrows 45E causes the valve 10 provide a flow of blood having spatially distributed equal velocities, represented by the arrows 45VE.

As shown in FIGS. 6 and 7, the rotor hub 34 has a plurality of slots 45 that extend parallel to the axis 17. When the valve 10 opens, the translation of the rotor hub 34 towards the collar 30, forces blood through the slots 45 away from the collar 30 to reduce stasis near the post 22. Similarly, when the valve 10 closes, the translation of the rotor hub 34 towards the stator hub 16, forces blood through the slots 45 towards the collar 30 to reduce stasis near the post 22.

It should be understood that because of the turbine-like construction of the valve 10, stress on the stator is equally distributed among the stator blades 12 and 14. Similarly, stress on the rotor is distributed among the rotor blades 36. The distribution of the stress reduces the probability of a fatigue failure of the valve 10. Moreover, in the remote possibility that one of the blades 12, 14 and 36 does break, the valve 10 is not completely inoperative.

It should be appreciated that the rotor is of small volume compared to corresponding structures of the prior art and is preferably constructed of durable lightweight material, whereby closure and opening of the valve 10 is faster and produces less noise than valves of the prior art. Additionally, the valve 10 has as many axes of symmetry as the sum of the blades 12, 14 and 36. The preferred embodiment has 16 axes of symmetry whereby the valve 10 is symmetrical for practical purposes. Hence, orientation of the valve 10 about the axis 17 is not of critical importance when the valve 10 is in the anatomic position.

Figure 13:
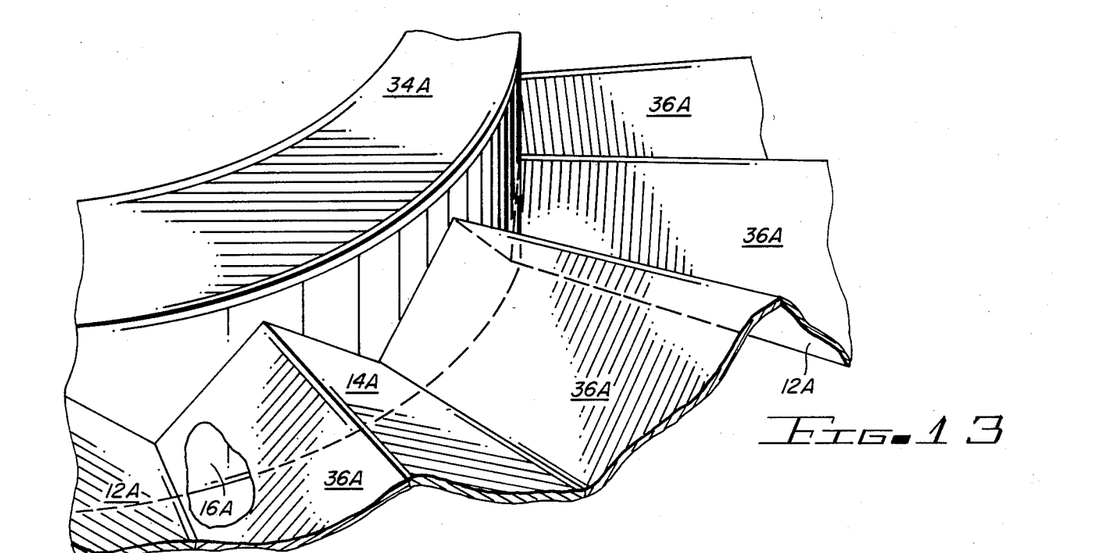
FIG. 13 is a partial isometric view showing, with portions broken away, elements of an artificial heart valve in accordance with an alternative embodiment of the present invention.

As shown in FIG. 13, an alternative embodiment of the present invention includes a stator hub 16A and a rotor hub 34A that have intermeshing opposed surfaces. The stator hub 16A is connected on its outside surface to stator blades 12A and 14A. Similarly, the rotor hub 34A is connected on its outside surface to rotor blades 36A. The intermeshing surfaces provide an increased area where the stator hub 16A is connected to the stator blades 12A and 14A. The increased areas of connection are similarly provided between the rotor hub 34A and the rotor blades 36A.

Figure 14:
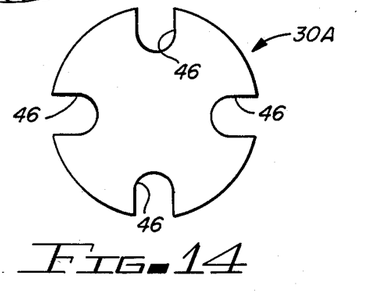
FIG. 14 is a plan view of an element of an artificial heart valve in accordance with an alternative embodiment of the present invention.

As shown in FIG. 14, in an alternative embodiment, a collar 30A has a plurality of slots 46, that extend parallel to the axis 17, to reduce the area of contact between opposed surfaces of the collar 30A and a rotor hub (not shown). The slots 46 additionally reduce stasis on the opposed surface of the rotor hub.

It should be understood that the rotor blades 36 are typically constructed with the largest portion of their surfaces at an angle of greater than 45 degrees and less than 90 degrees to the direction indicated by the arrow 38. The construction causes a greater force of translation than force of rotation to be applied to the rotor hub 34, via the blades 36, in response to the blood pressure in the direction indicated by the arrow 38. Therefore, the rotor hub 34 translates before it rotates. Inasmuch as the rotor hub 34 translates before it rotates, the rotor hub 34 cannot rotate past its closed position.

Figure 15:
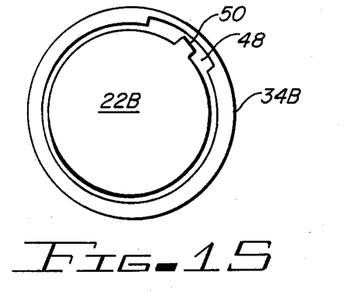
FIG. 15 is a plan view of elements of an artificial heart valve in accordance with an alternative embodiment of the present invention.

As shown in FIG. 15, in an alternative embodiment, closure of an artificial heart valve is assured by providing a rotor hub 34B with a longitudinal keyway 48 extending from its inside circumference. The keyway 48 receives a key 50 which is integral with a post 22B. The keyway 48 has an angular dimension selected to limit rotation of the rotor to its open and closed positions, thereby obviating the projections 15 and a need for criticality in the angle between rotor blades and the direction of blood pressure. Alternatively a hub, similar to the hub 34, can include a key; a post, similar to the post 22, would include the keyway. Other embodiments may include a plurality of pairs of keys and keyways to distribute stress.

In an alternative embodiment, the dimension of the keyway 48 is selected to substantially prevent rotation, whereby the rotor hub 34B can move only in translation relative to a stator.

The diameters of the hubs 16 and 34 are selected to provide desired fatigue resistant properties. In the prefered embodiment, the diameter of the hubs 16 and 34 is approximately one third of the inside diameter of the orifice ring 18. However, the hubs 16 and 34, only occlude approximately one ninth of the included area of the orifice ring 18 in a top view thereof.

In an alternative embodiment, an artificial heart valve, similar to the valve 10, is included as an element of either a dual or single chamber artificial heart. When included in the artificial heart, the suture ring 32 may not be used.

While the invention has been particularly shown and described with reference to preferred embodiments thereof, it should be understood by those skilled in the art that changes in the form and detail may be made therein without departing from the spirit and the scope of the present invention which is limited only by the appended claims.

What is claimed is:

1. An artificial heart valve, adapted for replacement of a heart valve of at least one of a human and an artificial heart, comprising:

means for securing the heart valve to a selected portion of the heart, said heart valve securing means including an orifice ring having an inlet aperture, an outlet aperture, a generally cylindrical channel operatively coupling said inlet aperture and said outlet aperture for defining an occludable space, said channel having a central longitudinal axis therethrough;

stator means including a plurality of stator blades operatively secured within said channel and secured against rotation therein;

rotor means including a plurality of rotor blades operatively disposed within said channel, said rotor blades being axially rotatable about said longitudinal axis and moveable in translation along said longitudingl axis, for substantially occluding and unoccluding said space in response to respective backward and forward differential blood pressures across said rotor means; and said stator means and said rotor means being substantially retained within said channel and said rotor blades being restrained from penetrating the plane of said inlet aperture and said outlet aperture in any of said occluded and said unoccluded positions, for providing a low profile valve, the rotation of said rotor means for occluding and unoccluding said space being substantially symmetrical about said longitudinal axis and about at least one axis in a plane normal to said longitudinal axis, said rotor means undergoing equal and opposite angular rotor displacements in the occluding and unoccluding rotational directions, respectively.

2. The artificial heart valve of claim 1 wherein said orifice ring is generally rigid and has an annular shape, said orifice ring being operably disposed in axial alignment with said longitudinal axis; and said plurality of stator blades includes "n" blades, where "n" $\geq 2$ and wherein each of said "n" blades is in the general shape of a turbine blade, the distal end of at least one of said "n" stator blades being fixedly connected to said orifice ring.

3. The artificial heart valve of claim 2 wherein said stator means additionally comprises a stator hub having a cone-shaped bottom for inhibiting stasis and a flat-faced top operably disposed in axial alignment with said longitudinal axis, said stator hub being connected to the proximal end of said "n" stator blades.

4. The artificial heart valve of claim 2 wherein said heart valve securing means additionally comprises a suture ring made from a porous fabric of generally annular construction, said suture ring being connected to the periphery of said orifice ring.

5. The artificial heart valve of claim 4 wherein said suture ring additionally includes a heat-shrinkable material adapted to be heat shrunk about the periphery of said orifice ring.

6. The artificial heart valve of claim 2 additionally comprising a thrombogenic resistant material selected from the group consisting of pyrolytic carbon and human, bovine and porcine pericardial tissue connected to said orifice ring such that there is substantially no wear on said tissue from either tissue flexion or mechanical tissue contact with the occluder to safely provide a substantially reduced probability of a thromboembolism and for substantially reducing the probability of excess endothelial tissue growth.

7. The artificial heart valve of claim 6 wherein said thrombogenic resistant material covers the surface of said orifice ring.

8. The artificial heart valve of claim 6 wherein said thrombogenic resistant material covers the interior surface and a portion of the exterior surface of said orifice ring.

9. The artificial heart valve of claim 6 additionally comprising a suture ring made from a porous fabric of generally annular construction connected to the periphery of said orifice ring, said thrombogenic resistant material covering at least a part of the interior surface of said orifice ring such that the margin between the orifice ring and said suture ring substantially eliminates the need for anticoagulants.

10. The artificial heart valve of claim 1 further including means for positively controlling the maximum angular displacement of said rotor blades about said longitudinal axis regardless of the blood flow pressure differential across said aperture.

11. An artificial heart valve adapted for replacement of a human heart valve, comprising:

stator means for providing an occludable space about an axis;

rotor means rotatable about and translatable along said axis for substantially occluding and unoccluding said space in response to respective backward and forward differential blood pressures across said rotor means;

said stator means further including a generally rigid annular orifice ring, said orifice ring being operably disposed in axial alignment with said axis;

said stator means including a plurality of stator blades, each of said stator blades being in the general shape of a turbine blade, the distal end of at least one of said stator blades being fixedly connected to the inner annular surface of said orifice ring; and said stator blades being equally spaced about said axis, a top projected view of the space between adjacent ones of said stator blades being substantially the same as the top projected view of said stator blades, a side projected view of said space, taken in the plane along the centerline of said space, being substantially the same as the side projected view of a stator blade taken in a plane along its centerline.

12. The artificial heart valve of claim 11 wherein said stator means additionally includes a post, said post comprising:
a top section of said post in the shape of a right truncated cone for inhibiting stasis; and
a bottom section of said post in the shape of a cylinder disposed coaxially with and longer than said top section and in axial alignment with said longitudinal axis, the distal end of said bottom section being integrally and coaxially connected to said top section.

13. A heart valve adapted for replacement of a human heart valve comprising:
stator means for providing an occludable space about a longitudinal axis;
rotor means axially rotatable about and moveable in translation along said longitudinal axis for substantially occluding and unoccluding said space in response to respective backward and forward differential blood pressures across said rotor means;
said rotor means further including an annular rotor hub; and
a plurality of rotor blades, each in the general shape of a turbine blade, the proximal ends of said rotor blades being connected to said rotor hub.

14. The artificial heart valve of claim 13 wherein said stator means includes a post having a top section in the shape of a right truncated cone for minimizing stasis connected to the proximal end of a bottom section having the shape of a cylinder, a collar having a flat bottom connected to said top section, a stator hub connected to the distal end of said bottom section, all of said stator means, said post, said cone, said cylinder, said collar, and said stator hub being coaxial with said longitudinal axis, said rotor hub being mounted on said post for rotation about said longitudinal axis.

15. The artificial heart valve of claim 14 wherein said rotor hub has a plurality of slots in its interior surface that extend parallel to said axis, translation of said rotor hub towards said collar forcing blood through said slots away from said collar, translation of said rotor hub towards said stator hub forcing blood through said slots towards said collar.

16. The artificial heart valve of claim 14 wherein said bottom section is longer than said top section.

17. The artificial heart valve of claim 14 wherein said stator and rotor hubs have intermeshing surfaces.

18. The artificial heart valve of claim 14 wherein said collar has a plurality of slots that extend parallel to said longitudinal axis.

19. The artificial heart valve of claim 14 wherein said rotor hub has a longitudinal keyway extending from its inside circumference, additionally comprising a key connected to said post, said key and keyway operating to limit rotation of said rotor to positions that cause said rotor blades to occlude said space.

20. The artificial heart valve of claim 14 wherein the largest portion of the surface of said rotor blades is at an angle greater than 45 degrees but less than 90 degrees with the direction of the flow of blood through said valve.

21. The artificial heart valve of claim 14 wherein said plurality of stator blades are connected to said stator hub, said rotation and translation to cause said valve to close being limited by contact between an edge of at least one of said plurality of stator blades and an edge of at least one of said plurality of rotor blades.

22. The artificial heart valve of claim 21 additionally comprising a projection means operatively coupled to at least one of said plurality of stator blades, said projection means contacting an edge of at least one of said plurality of rotor blades to limit the rotation of said rotor hub when said valve is open.

23. The artificial heart valve of claim 21 wherein said plurality of rotor blades includes "m" rotor blades, where "m"$\geq$2 and where "m" is a positive whole number, each of said "m" blades being in the general shape of a turbine blade, the proximal ends of said "m" rotor blades being operably connected to said rotor hub, said stator means including a plurality of "n" blades where "n"$\geq$2 and where "n" is a positive whole number, and wherein each of said "n" blades is in the general shape of a turbine blade, the distal end of at least one of said "n" stator blades being fixedly coupled to said orifice ring means, and wherein "n"="m".

24. A valve for at least one of a human and an artificial heart, comprising:
means for providing an occludable space about a central axis; and
an axially rotatable occluder means for substantially occluding and unoccluding said space in response to respective backward and forward differential blood pressures across said occluder means; and
said occluder means being moveable with respect to said space-providing means, said occluder means being substantially symmetrical with respect to said space-providing means at least along said axis, the angular rotation of said occluder means with respect to said space-providing means being relatively independent of the magnitude of the blood flow rate through the occludable space but being controlled by said occluder means to insure equal and opposite angular rotation thereof in both occluding and unoccluding directions.

25. An artificial heart valve having a suture ring connected to the periphery of an orifice ring, comprising:
a plurality of stator blades, each in the general shape of a turbine blade, the distal end of at least one of said stator blades being connected to said orifice ring with equal spaces between adjacent stator blades;

a stator hub coaxially disposed relative to said orifice ring, said stator hub being connected to the proximal ends of said stator blades;

a post, having a top section in the shape of a right truncated cone and a bottom section in the shape of a cylinder, ends of said bottom section being coaxially connected to said top section and said stator hub, respectively;

a key connected to said bottom section;

a generally annular rotor hub having a keyway that receives said key;

a plurality of rotor blades connected to said rotor hub, said rotor hub being rotatable about said post and moveable in translation to cause said rotor blades to occlude and unocclude said spaces; and a collar having a flat bottom, coaxially connected to said post, translation of said rotor being limited by said stator blades and the flat bottom of said collar.

26. The artificial heart valve of claim 25 wherein said keyway has a dimension selected to substantially prevent rotation of said rotor hub.

27. In the method of controlling a flow of blood in a heart, the steps of:

providing an occludable space between adjacent ones of a plurality of stator blades disposed about a central axis;

rotating a rotor about said axis and translating said rotor along said axis to cause a plurality of rotor blades to occlude and unocclude said space in response to respective backward and forward differential blood pressures across said rotor.

28. An artificial heart valve, adapted for replacement of an exised human valve, comprising:

an annular orifice ring for attachment to the heart, said orifice ring having an inlet, an outlet, and a chamber interconnecting the inlet and outlet along the longitudinal axis thereof;

stator means including a stator hub operably disposed within said chamber and aligned with said longitudinal axis, said stator means further including a plurality of spatially separated, equally spaced stator blades each having its radially inward distal end portion fixedly secured to said rotor hub and at least one of said stator blades having its radially outer distal end portion fixedly secured to the inner annular wall of said orifice ring to prevent rotation of said stator hub with respect to said orifice ring;

rotor means including a rotor hub operably disposed within said chamber and aligned with said longitudinal axis, said rotor means further including a plurality of spatially separated, equally-spaced rotor blades each having their radially inward distal end portion fixedly secured to said rotor hub for rotation therewith; and means for operably coupling said rotor means to said stator means along said longitudinal axis for rotation of said rotor means about said longitudinal axis and for translation along said longitudinal axis toward and away from said stator means for substantially occluding said chamber in response to a differential blood pressure in a backward direction across said rotor means to close the artificial heart valve and for substantially unoccluding said space in response to a differential blood pressure in a forward direction across said rotor means to open said artificial heart valve.

29. An artificial heart valve adapted for replacement of an excised human heart valve comprising, in combination:

an annular orifice ring for attachment to said heart and including means for defining an occludable space having a longitudinal axis;

stator means operably disposed substantially within said orifice ring and aligned with said axis, said stator means secured against rotation within said orifice ring;

rotor means constrained substantially entirely within said occludable space within said orifice ring for rotation and translation about and along said axis without contacting said orifice ring, said rotor means for substantially occluding and unoccluding said occludable space in response to differential blood pressures across said valve.

30. A method of controlling the flow of blood in a heart comprising the steps of:

providing an occludable space about an axis;

rotating an occluder such that the angular rotation of the occluder is relatively independent of the magnitude of blood flow through the space;

occluding and unoccluding the space in response to the differential blood pressure across the space; and controlling the angular rotation of the occluder to insure equal and opposite rotations of the occluder in both the occluding and unoccluding directions.

31. A method of controlling a flow of blood in an artificial heart comprising the steps of:

providing an occludable space between adjacent ones of a plurality of stator blades disposed about a central axis; and rotating a rotor about said axis and translating the rotor along said axis to cause a plurality of rotor blades to occlude and unocclude said space in response to respective backward and forward differential blood pressures across said rotor.

* * * * *